(12) United States Patent
Hestad et al.

(10) Patent No.: US 7,947,045 B2
(45) Date of Patent: May 24, 2011

(54) SPINAL STABILIZATION SYSTEM WITH FLEXIBLE GUIDES

(75) Inventors: Hugh Hestad, Edina, MN (US); Mark Rice, Minneapolis, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 745 days.

(21) Appl. No.: 11/539,287

(22) Filed: Oct. 6, 2006

(65) Prior Publication Data

US 2008/0161857 A1 Jul. 3, 2008

(51) Int. Cl.
*A61B 17/70* (2006.01)

(52) U.S. Cl. .................. 606/86 A; 606/99; 606/104

(58) Field of Classification Search .......... 606/246–279, 606/86, 300–321, 86 A, 96, 99, 104
See application file for complete search history.

(56) References Cited

U.S. PATENT DOCUMENTS

| | | | |
|---|---|---|---|
| 5,030,220 A | 7/1991 | Howland |
| 5,540,688 A | 7/1996 | Navas |
| 5,562,660 A | 10/1996 | Grob |
| 5,584,831 A | 12/1996 | McKay |
| 6,290,700 B1 | 9/2001 | Schmotzer |
| 6,530,929 B1 | 3/2003 | Justis et al. |
| 6,986,771 B2 | 1/2006 | Paul et al. |
| 6,989,011 B2 | 1/2006 | Paul et al. |
| 7,008,424 B2 | 3/2006 | Teitelbaum |
| 7,326,210 B2 | 2/2008 | Jahng et al. |
| 2002/0035366 A1 | 3/2002 | Walder et al. |
| 2005/0065516 A1 | 3/2005 | Jahng |
| 2005/0085813 A1* | 4/2005 | Spitler et al. ............ 606/61 |
| 2005/0085815 A1 | 4/2005 | Harms et al. |
| 2005/0124991 A1 | 6/2005 | Jahng |
| 2005/0131408 A1 | 6/2005 | Sicvol et al. |
| 2005/0143737 A1 | 6/2005 | Pafford et al. |
| 2005/0154390 A1 | 7/2005 | Biedermann et al. |
| 2005/0192570 A1 | 9/2005 | Jackson et al. |
| 2005/0203513 A1 | 9/2005 | Jahng et al. |
| 2005/0245929 A1 | 11/2005 | Winslow et al. |
| 2006/0111715 A1* | 5/2006 | Jackson ............ 606/61 |
| 2006/0142758 A1 | 6/2006 | Petit |
| 2007/0016200 A1 | 1/2007 | Jackson |
| 2007/0055244 A1 | 3/2007 | Jackson |
| 2007/0106123 A1 | 5/2007 | Gorek et al. |
| 2007/0129729 A1 | 6/2007 | Petit et al. |
| 2007/0198088 A1 | 8/2007 | Biedermann et al. |
| 2007/0270860 A1 | 11/2007 | Jackson |
| 2007/0293862 A1 | 12/2007 | Jackson |
| 2007/0299443 A1 | 12/2007 | DiPoto et al. |

(Continued)

FOREIGN PATENT DOCUMENTS

EP 0-669-109 B1 8/1995

(Continued)

*Primary Examiner* — Eduardo C Robert
*Assistant Examiner* — Christina Negrelli
(74) *Attorney, Agent, or Firm* — Seager, Tufte & Wickhem, LLC

(57) ABSTRACT

In one embodiment, a spinal stabilization apparatus includes a vertebral anchor having a head portion and a bone attachment portion. An elongate, flexible guide is removably coupled to the head portion of the vertebral anchor and has a channel extending longitudinally thereof and communicating with a slot in the head portion of the anchor. An elongate cord may be received within the channel to facilitate inserting and securing a spacer between pairs of anchors installed into adjacent vertebrae of a person's spine.

29 Claims, 10 Drawing Sheets

U.S. PATENT DOCUMENTS

| | | |
|---|---|---|
| 2008/0082103 A1 | 4/2008 | Hutton et al. |
| 2008/0091213 A1 | 4/2008 | Jackson |
| 2008/0114403 A1 | 5/2008 | Kuester et al. |
| 2008/0119849 A1 | 5/2008 | Beardsley et al. |
| 2008/0140076 A1 | 6/2008 | Jackson |
| 2008/0262318 A1 | 10/2008 | Gorek et al. |
| 2008/0300638 A1 | 12/2008 | Beardsley et al. |

FOREIGN PATENT DOCUMENTS

| | | | |
|---|---|---|---|
| EP | 0669109 | A1 | 8/1995 |
| EP | 0669109 | B1 | 5/1999 |
| EP | 1523949 | A1 | 4/2005 |
| EP | 1523949 | B1 | 6/2007 |
| FR | 2715057 | A1 | 7/1995 |
| FR | 2844180 | A1 | 3/2004 |
| FR | 2867057 | A1 | 9/2005 |
| NL | 7610576 | | 3/1978 |
| WO | 9417745 | A1 | 8/1994 |
| WO | 9519149 | A1 | 7/1995 |
| WO | 9905980 | A1 | 2/1999 |
| WO | 2004-004549 | A2 | 1/2004 |
| WO | 2004024011 | A1 | 3/2004 |
| WO | 2005087121 | A1 | 9/2005 |
| WO | 2006066685 | A1 | 6/2006 |

* cited by examiner

SPINAL STABILIZATION SYSTEM WITH FLEXIBLE GUIDES

TECHNICAL FIELD

The present invention relates generally to spinal support devices, and more particularly to devices that facilitate installing an implantable system for providing dynamic stability of a person's spine.

BACKGROUND OF THE INVENTION

The treatment of acute and chronic spinal instabilities or deformities of the thoracic, lumbar, and sacral spine has traditionally involved the implantation of rigid rods to secure the vertebrae of a patient. More recently, flexible materials have been utilized in connection with securing elements, such as pedicle screws, to provide a dynamic stabilization of the spine. Such dynamic stabilization systems typically include a flexible spacer positioned between pedicle screws installed in adjacent vertebrae of person's spine. Once the spacer is positioned between the pedicle screws, a flexible cord is threaded through eyelets formed in the pedicle screws and an aperture through the spacer. The flexible cord retains the spacer between the pedicle screws while cooperating with the spacer to permit mobility of the spine. One drawback of traditional implantation of such dynamic stabilization systems is that relatively large surgical sites are required to permit threading the cord through the screws and spacer once the spacer has been positioned between the screws.

While some dynamic stabilization systems have been proposed for permitting the top loading of a spacer and cord between pedicle screws using guide rods to direct the cord and spacer between the screws, these systems also require a relatively large surgical sites and present difficulties when the curvature of the spine causes a convergence of the guide rods that makes it difficult to position the spacer between the guide rods.

A need therefore exists for a spinal dynamic stabilization system that overcomes these and other drawbacks of the prior art.

SUMMARY OF THE INVENTION

The present invention overcomes the foregoing and other shortcomings and drawbacks of spinal stabilization systems heretofore known for use in suitable various commercial and industrial environments. While various embodiments will be described herein, it will be understood that the invention is not limited to these embodiments. On the contrary, the invention includes all alternatives, modifications and equivalents as may be included within the spirit and scope of the present invention.

In one embodiment, a spinal stabilization apparatus includes a vertebral anchor having a head portion and a bone attachment portion. A slot in the head portion has an open end opposite the bone attachment portion. The apparatus further includes an elongate, flexible guide removably coupled to the head portion of the vertebral anchor. A longitudinally extending channel in the guide communicates with the slot in the head portion of the anchor, through the open end thereof.

The apparatus may further include an elongate, flexible cord sized to be received in the channel. The cord may thereby be directed along the channel and received within the slot of the head portion. A securing member may be coupled to the head portion to retain the cord within the slot. The securing member may be carried on a portion of the guide until it is needed to secure the cord within the slot.

In another embodiment, the flexible guide may be formed from polymeric material. The polymeric material may be integrally molded to the head of the vertebral anchor, or it may be molded separately and thereafter secured to the head of the vertebral anchor. In yet another embodiment, at least part of the guide proximate the head portion of the vertebral anchor is non-polymeric, while the rest of the guide comprises polymeric material.

In another embodiment, an implantable spinal apparatus includes first and second vertebral anchors, each comprising a head portion and a bone attachment portion. Elongate, flexible guides are removably coupled to the head portions of respective anchors. Each guide includes a channel extending longitudinally thereof and communicating with a slot formed in the head portion of the respective anchor. An elongate, flexible cord extends through the channels of the guides and through a spacer disposed between the guides. The cord and spacer may be directed along the guides and the cord may be received within the slots to position the spacer between the vertebral anchors. The apparatus further includes securing members associated with the vertebral anchors for retaining the cord within the slots of the respective anchors.

In yet another embodiment, a method of stabilizing a spine through an incision includes securing at least first and second anchors to respective first and second vertebrae, coupling a spacer to an elongate cord, directing the cord between guides extending from the anchors, flexing the anchors to receive the spacer therebetween, directing the cord and spacer along the guides to an installation position between the anchors, and removing the guides from the anchors.

These and other features, objects and advantages of the invention will become more readily apparent to those skilled in the art in view of the following detailed description, taken in conjunction with the accompanying drawings.

BRIEF DESCRIPTION OF THE DRAWINGS

The accompanying drawings, which are incorporated in and constitute a part of this specification, illustrate embodiments of the invention and, together with the general description of the invention given above, and the detailed description given below, serve to explain the principles of the invention.

DETAILED DESCRIPTION

Figure 1:
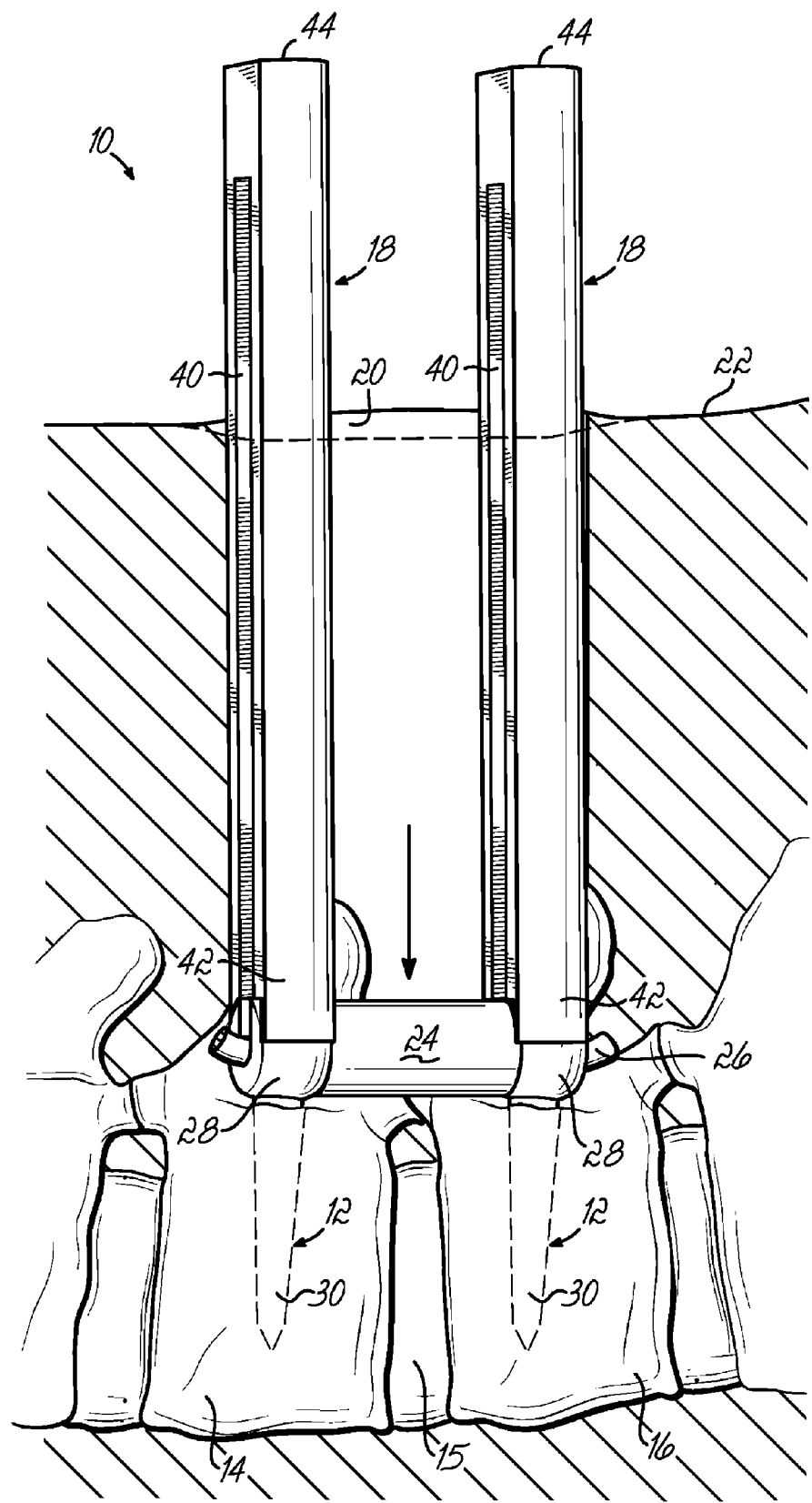
FIG. 1 is a partial section view of the human spinal region illustrating an exemplary stabilization apparatus in accordance with one embodiment.

FIG. 1 depicts a portion of a human spine, with adjacent vertebrae 14, 16 separated by a disc 15. FIG. 1 also illustrates one embodiment of a spinal stabilization system 10 comprising anchors 12 installed into adjacent vertebrae 14, 16 of the spine using flexible, removable guides 18 inserted through a minimally invasive incision 20 formed through the patient's skin 22. In the embodiment shown, at least two anchors 12, shown here in the form of pedicle screws, are fixedly installed into the pedicle area of adjacent vertebrae 14, 16 and a flexible spacer 24 is disposed therebetween to control abnormal motion of the spine, while otherwise leaving the spinal segment mobile. The spacer 24 and pedicle screws 12 are coupled together by a flexible cord 26 threaded through the spacer 24 and secured to the heads 28 of the screws 12. Such spacers 24 and cords 26 may be similar to those used in the Dynesys® Dynamic Stabilization System available from Zimmer, Inc. of Warsaw, Ind. In one embodiment, the spacer 24 may be formed from polycarbonate urethane and the cord 26 may be formed from polyethylene-terephthalate, although it will be recognized that various other materials suitable for implantation within the human body and for providing stabilization of the spine while maintaining flexibility may be used.

FIGS. 2A, 2B and 3-5 depict the exemplary combination anchor/guide of FIG. 1 in more detail. In this embodiment, the anchor 12 comprises a pedicle screw having a threaded shank portion 30 configured to be screwed into the pedicle area of a vertebra. A head portion 28 of the screw is configured to receive and secure the flexible cord 26. In the embodiment shown, the head 28 includes a slot 32 extending generally transverse to the longitudinal axis 34 of the shank portion 30 and having an open end 36 opposite the shank portion 30 for receiving the flexible cord 26 into the slot 32 of the head 28 in a top loading fashion. Accordingly, the open-ended slot 32 alleviates the need to thread the cord 26 into the head 28 of the anchor 12 after the anchor 12 has been installed into the vertebral body of a patient's spine. In this embodiment, the head 28 of the pedicle screw 12 has generally flat faces 33 provided on oppositely disposed sides of the head 28 to facilitate screwing the device into a vertebra of a patient's spine using a driving tool (not shown). In one embodiment, the pedicle screw 12 is formed from a titanium alloy, but it will be recognized that various other materials suitable for implantation within the human body and having sufficient strength to be securely attached to the bone and to secure the flexible cord 26 may be used. While a uniaxial pedicle screw is shown and described herein, it will be recognized that the anchor 12 may alternatively comprise a hook, a polyaxial pedicle screw, or various other structure suitable to be secured to a vertebral body.

An elongate guide 18 is removably secured to the head portion 28 of the pedicle screw 12 and is formed substantially from a resilient, flexible material that permits deformation or bending of the guide 18 along its length without transmitting significant force to the pedicle screw 12. For example, the guide 18 may be formed from polymeric material such as nylon, polyethylene, polyurethane, or various other polymeric materials which are biocompatible and provide sufficient flexibility to permit the guides to bend in flexure along their length without transmitting significant force to the pedicle screw 12. In the embodiment shown, the guide 18 includes a longitudinal channel 40 extending from a first end 42 toward a second end 44 of the guide 18. The channel 40 has an opening 46 at the first end 42 that is shaped to mate with the head 28 of the pedicle screw 12 such that the channel 40 communicates with the slot 32 formed in the head 28 of the pedicle screw 12. In this arrangement, the longitudinally extending channel 40 may be used to guide a flexible cord 26 from the second end 44 of the guide 18, along its length, and into the slot 32 formed in the head 28 of the pedicle screw 12.

In one embodiment, the guide 18 is integrally molded onto the head 28 of the pedicle screw 12. Mating surfaces between the pedicle screw and the guide are configured to provide a mechanical interlock that is sufficient to withstand forces applied to the guides 18 during installation of the pedicle screws 12 into the vertebrae 14, 16 and installation of the spacer 26 between adjacent pedicle screws 12. However, the guides 18 may be removed from the heads 28 of the pedicle screws 12, for example, by application of an appropriate force or by manipulating the guide 18 relative to the pedicle screw 12, to cause the guide 18 to become separated from the head 28 of the pedicle screw 12. The guide 18 may be integrally molded onto the head 28 of the pedicle screw 12, for example, by a molding process wherein the pedicle screw 12 is placed into a mold and the material forming the guide 18 is injected or otherwise transferred into an adjacent cavity to form the guide 18 directly onto the head 28 of the pedicle screw 12. Alternatively, the guide 18 may be formed in a molding process without the pedicle screw 12, and may thereafter be joined to the head 28 of the pedicle screw 12 by bonding or mechanically interlocking the guide 18 onto the head 28 the pedicle screw 12.

FIGS. 2A, 2B and 3-5 illustrate an exemplary embodiment wherein the guide 18 is integrally molded onto the head 28 of the pedicle screw 12. In this embodiment the first end 42 of guide 18 has first and second oppositely disposed, downwardly extending fingers 50a, 50b, one provided on each side of channel 40. The fingers 50a, 50b have laterally inwardly facing protrusions 52a, 52b for engaging corresponding apertures 54a, 54b formed on opposite sides of the head 28. The protrusions 52a, 52b mechanically lock the first end 42 of the guide 18 to the head 28. When it is desired to remove the guide 18 from the head 28, a user applies a force to the second end 44 of the guide 18, generally in a direction that causes longitudinal bending of the guide 18 about an axis 56 through slot 32 in the head 28. When the designed release load is reached, one protrusion (52a, for example) will break free from its corresponding aperture 54a and the protrusion 52a and finger 50a will slide up an inclined face 58a between the aperture 54a and the top end 60 of head 28. The other protrusion 52b may be released from its corresponding aperture 54b by bending the guide 18 in an opposite direction so that finger 50b and protrusion 52b slide up inclined face 58b. With protrusions 52a, 52b free of apertures 54a, 54b, guide 18 can be withdrawn away from head 28.

Figure 2A:
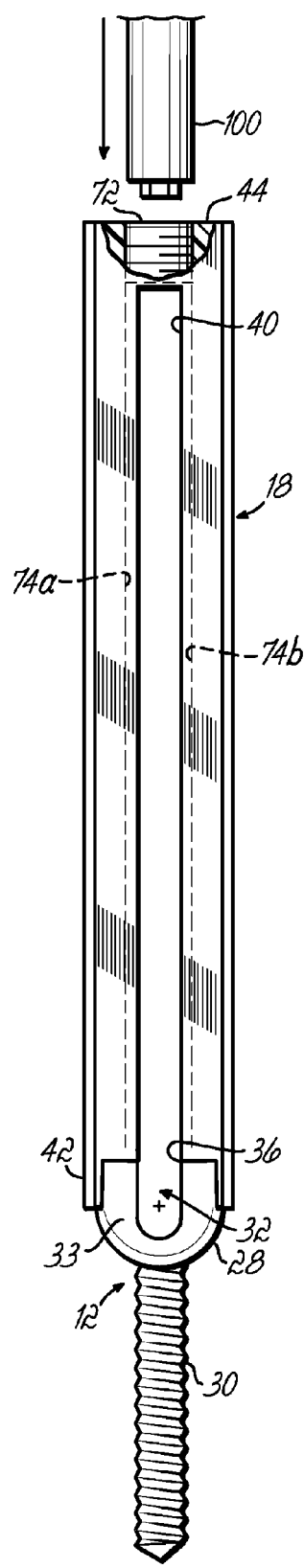
FIG. 2A-2B are side elevation views depicting an exemplary anchor/guide of the apparatus of FIG. 1.
Figure 2B:
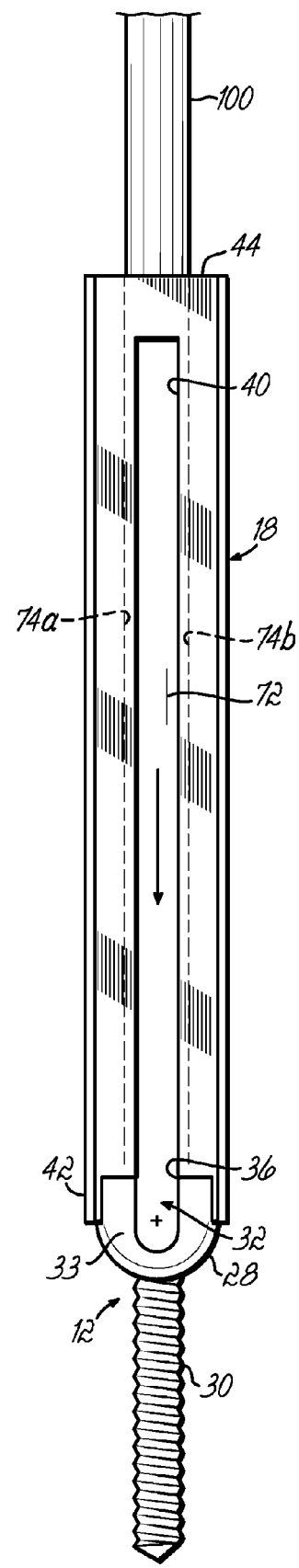
Figures 3, 3A:
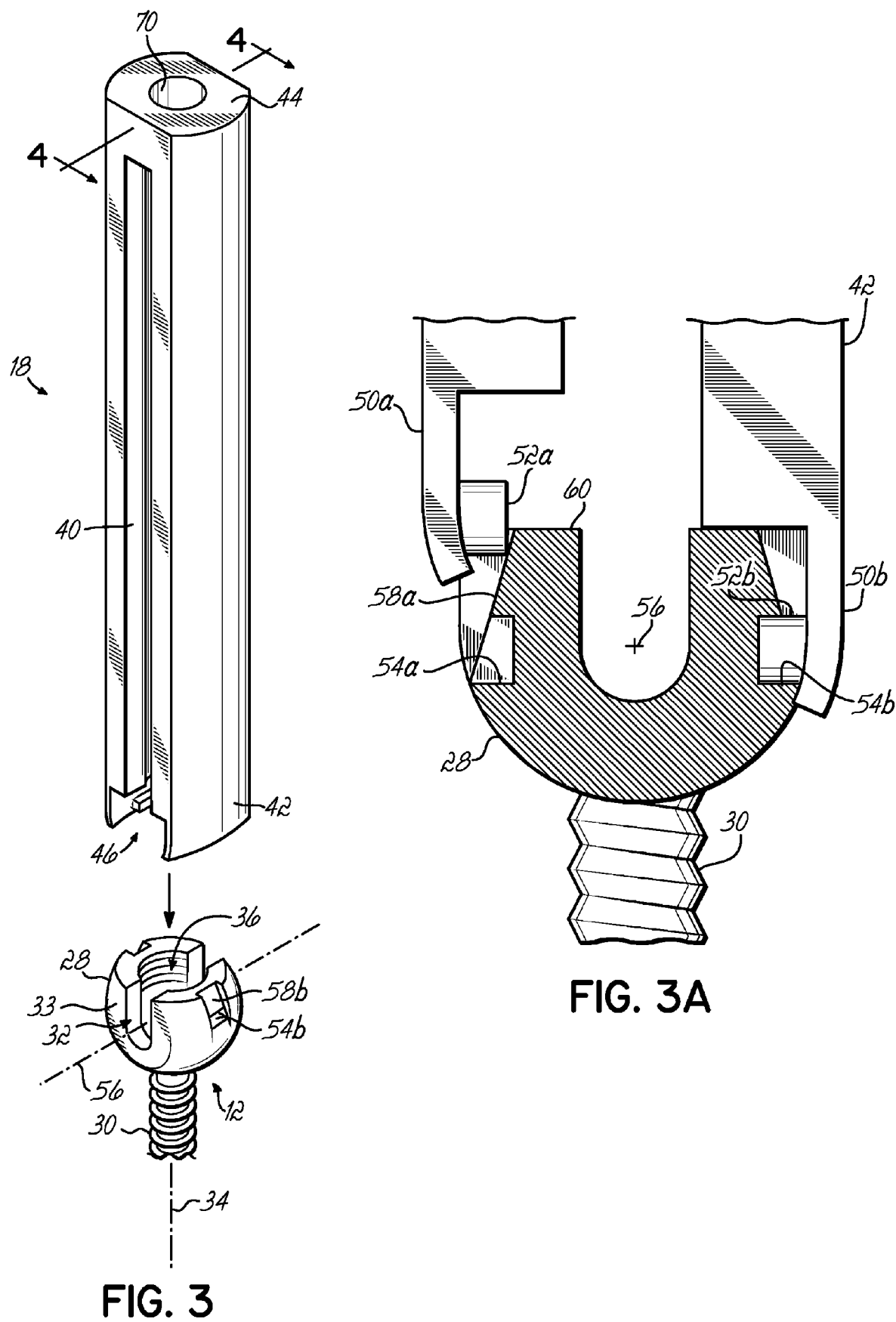
FIG. 3 is an exploded perspective view of the anchor/guide of FIGS. 2A-2B.
FIG. 3A is a detail cross-sectional view of the head portion of the anchor/guide of FIGS. 2A-2B, illustrating removal of the guide.
Figure 4:
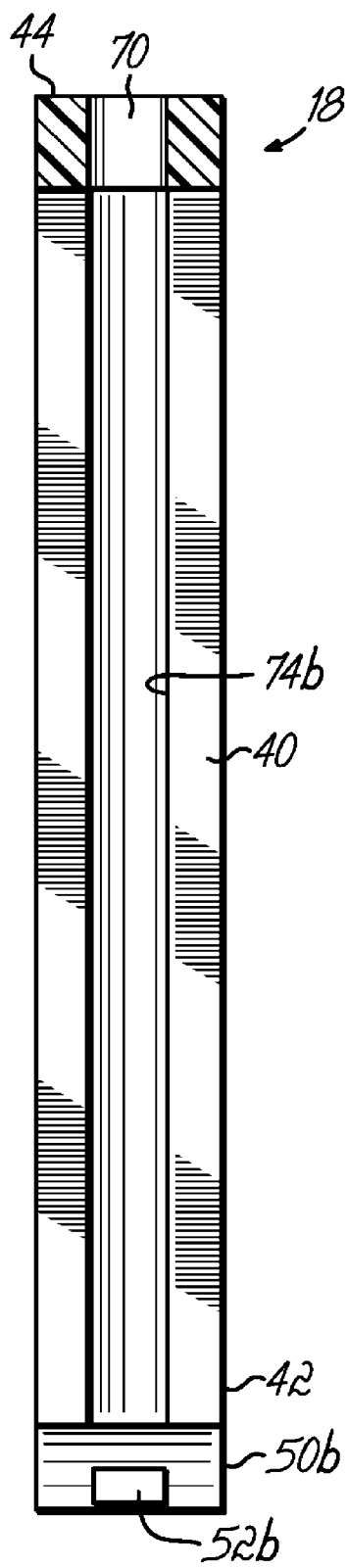
FIG. 4 is a cross-sectional view taken along line 4-4 of FIG. 3.
Figure 5:
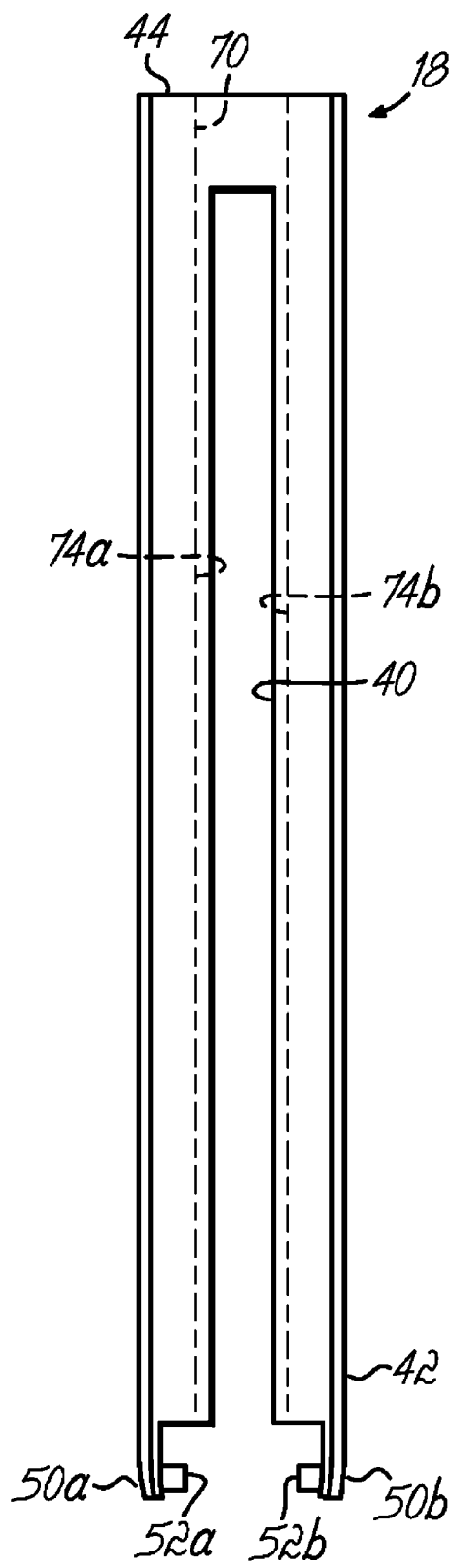
FIG. 5 is a side elevation view of the guide rod of FIGS. 2A-2B.

With continued reference to FIGS. 2A, 2B and 3-5, the guide 18 may further include an aperture 70 proximate the second end 44 for receiving and retaining a securing member 72, such as a set screw, for securing the cord 26 to the head of the pedicle screw 12, as will be described more fully below. When the guides 18 comprise polymeric material, the securing member 72 may be molded in the aperture 70 when the guides are formed. Alternatively, the securing members 72 may be coupled to the guides 18 after they are formed. Longitudinally extending grooves 74a, 74b may be formed on the inwardly facing surfaces of the guide 18 which are defined by the longitudinally extending channel 40. The grooves 74a, 74b are sized to direct the securing member 72 along the length of the guide 18 and into engagement with the head 28 of the pedicle screw 12 when it is desired to secure the cord 26 to the head 28 of the pedicle screw 12. In one embodiment, a driver 100 or other tool suitable for engaging the securing member, or set screw, 72 may be inserted through aperture 70 to dislodge the securing member 72 from the aperture and direct the securing member 72 along grooves 74a, 74b into engagement with the threaded open end 36 of the head 28 of pedicle screw 12, as depicted in FIGS. 2A-2B.

While the securing member 72 has been shown and described herein as comprising a set screw, it will be recognized that various other types of securing members may alternatively be used to secure the cord 26 to the head 28 of an anchor 12. Likewise, in place of aperture 70, the guide 18 may be configured to accommodate these various other types of securing members and to retain them until it is desired to engage the securing member 72 with the anchor 12.

Figure 6:
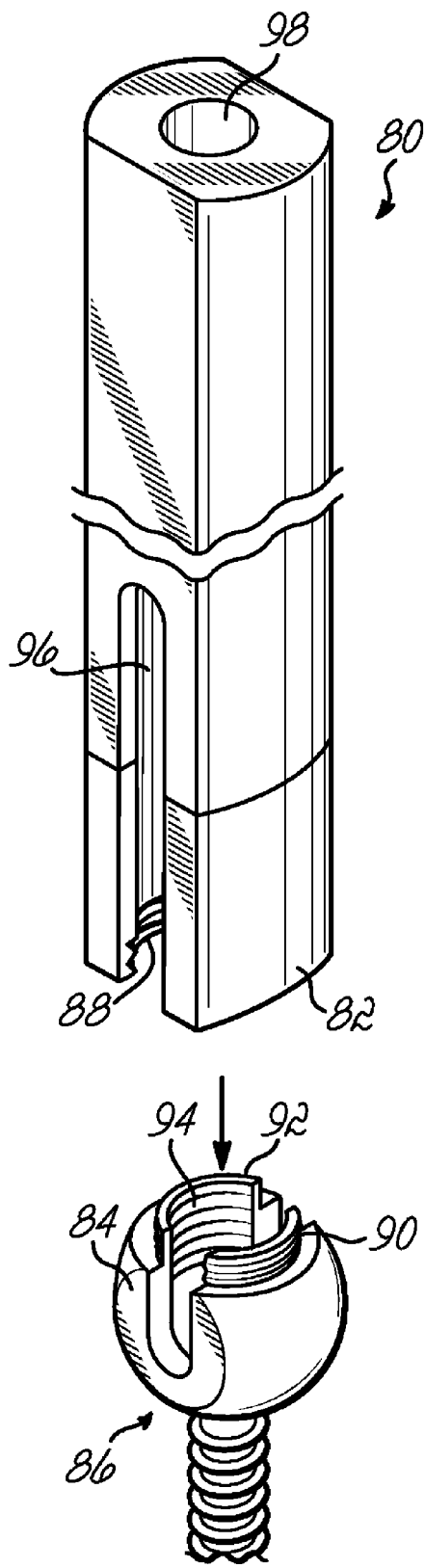
FIG. 6 is an exploded perspective view of another exemplary anchor/guide, similar to FIG. 3.
Figure 7:
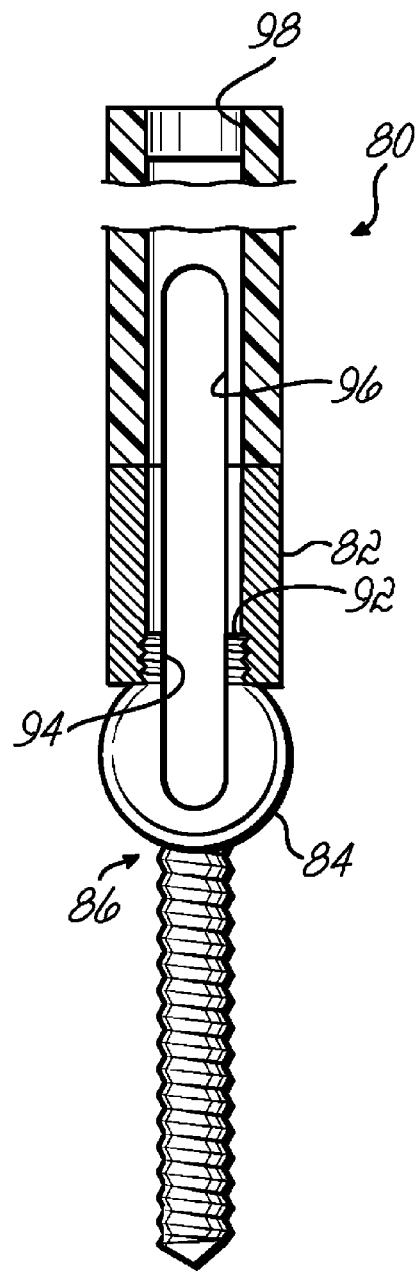
FIG. 7 is a partial cross-sectional elevation of the assembled anchor/guide of FIG. 6.

In another exemplary embodiment, a guide may be configured as a composite structure, comprising a first portion formed from a substantially rigid material and a second portion comprising a flexible material. In the embodiment shown in FIGS. 6-7, guide 80 is similar to the guide 18 discussed above, except the first end 82 of the guide 80 is formed from metal while the rest of the guide 80 is formed from a flexible polymeric material similar to that described above. The first end 82 of the guide 80 is constructed to provide a releasable attachment to the head 84 of the pedicle screw 86. In the embodiment shown, the guide 80 includes internal threads 88 formed on confronting surfaces of the first end 82 for engaging correspondingly formed external threads 90 provided on protrusions 92 extending upwardly from the open end 94 of the head 84 of the pedicle screw 86. The flexible portion of guide 80 may further include an elongate channel 96 and an aperture communicating with channel 96, as well as various other features shown and described above with respect to guide 18. In this embodiment, the flexible guide 80 may be removed from the head 84 of the pedicle screw 86 by rotating the guide 80 about its longitudinal axis to thereby unthread the guide 80 from the pedicle screw 86. Alternatively, the metal first end 82 may be secured to the head 84 of the pedicle screw 86 by laser welding or various other methods to provide a frangible attachment having sufficient strength to withstand installation forces while being capable of removal from the pedicle screw 86 once installation is complete.

Figure 8:
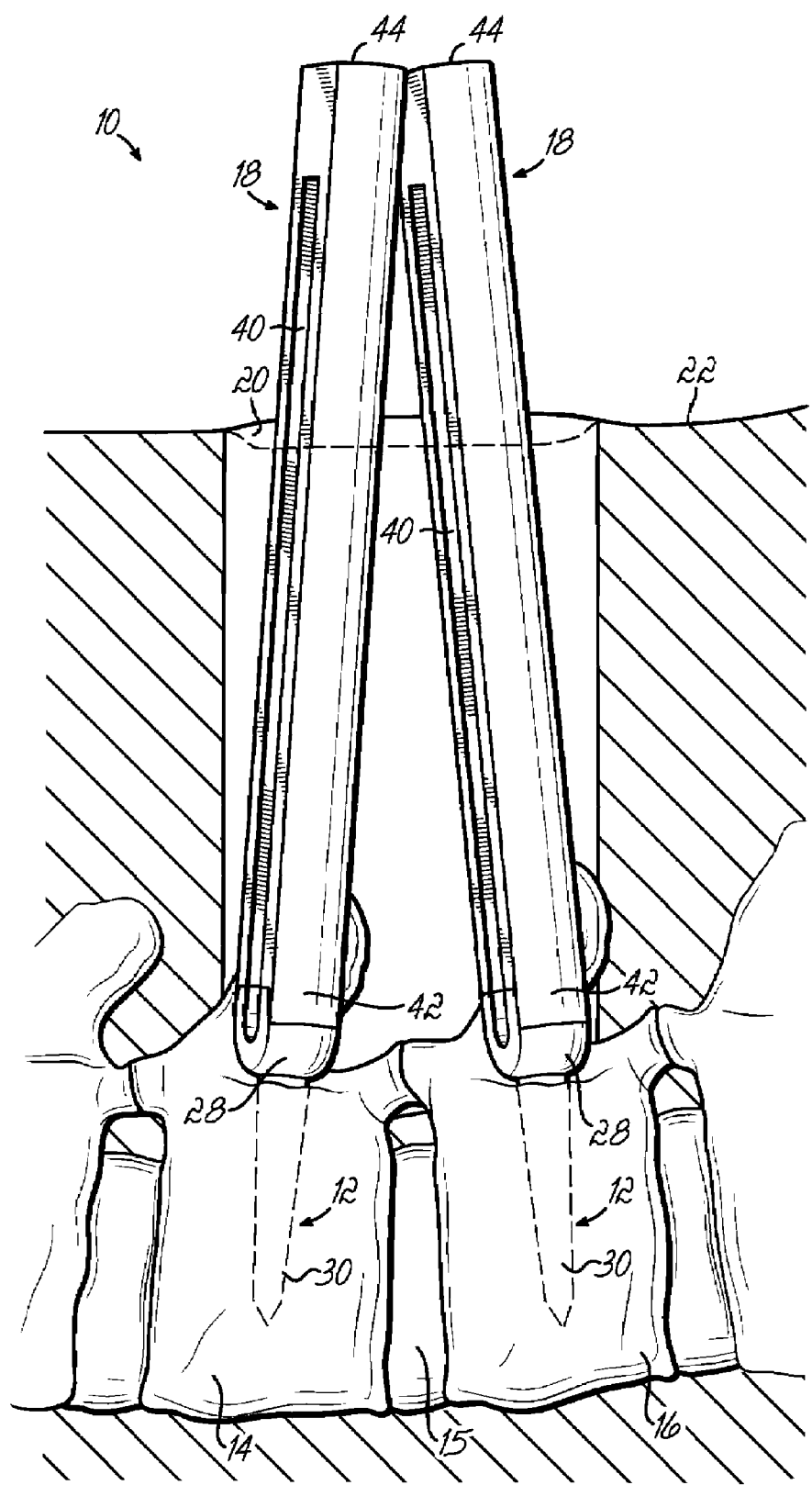
FIG. 8 is a partial section view, similar to FIG. 1, illustrating anchor/guides installed into adjacent vertebrae.
Figure 8A:
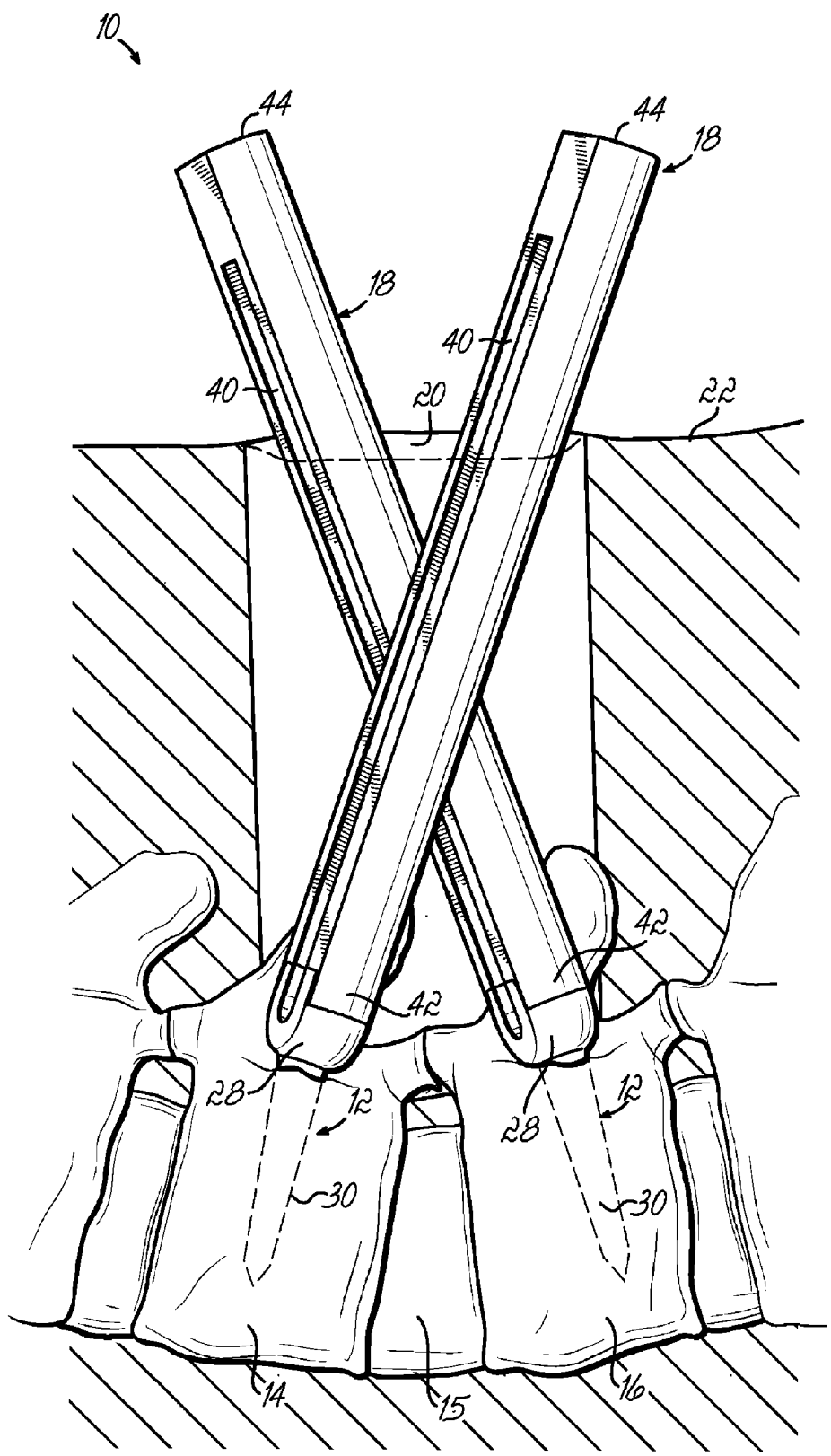
FIG. 8A is a partial section view, similar to FIG. 8, illustrating anchor/guides installed into a curved region of a spine.
Figure 9:
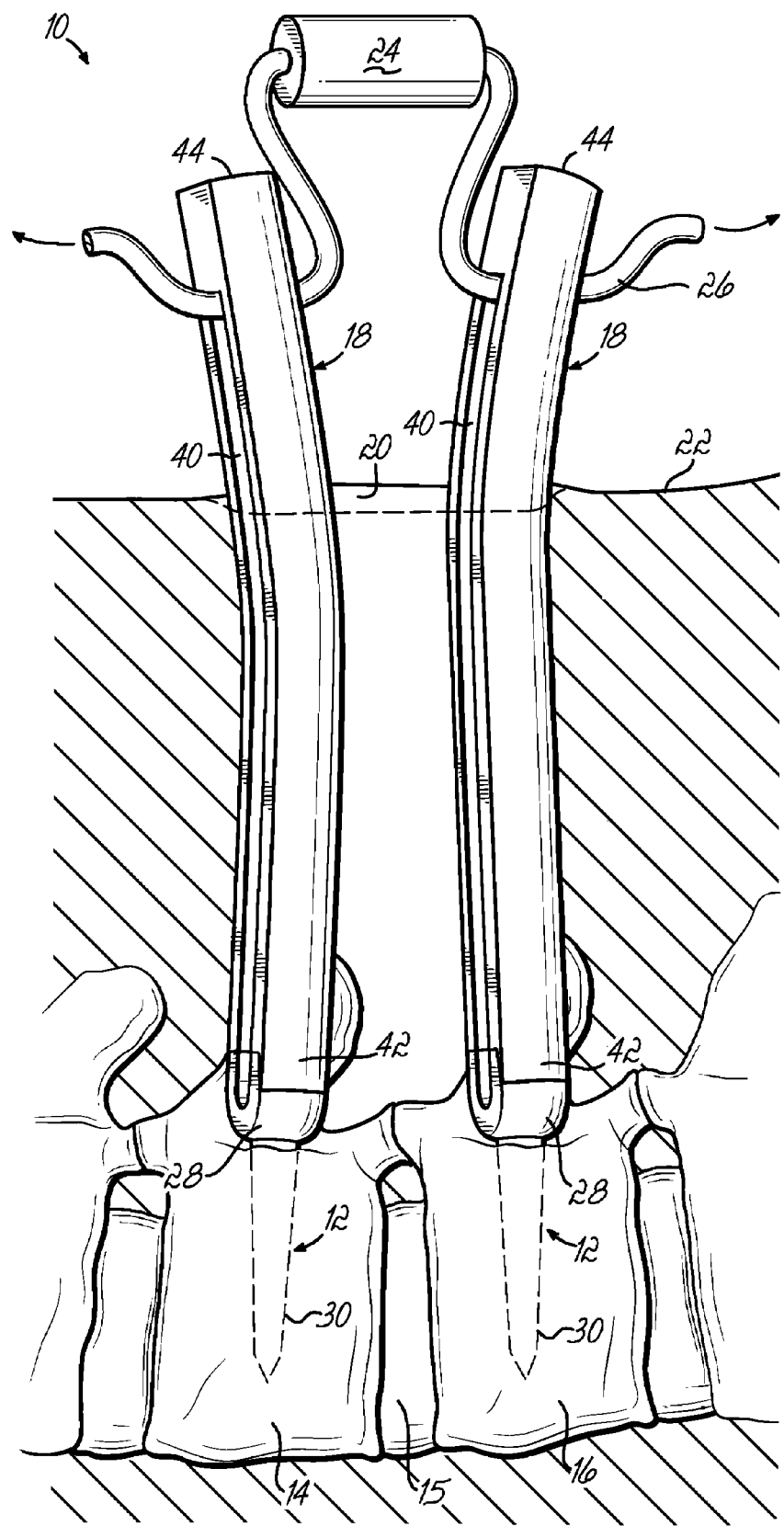
FIG. 9 illustrates the apparatus of FIG. 8 further including a spacer and flexible cord.

Referring now to FIGS. 1, 8, 8A and 9-11, use of the anchor/guide of FIGS. 2A, 2B and 3-5 to install a spinal stabilization device 10 to adjacent vertebrae 14, 16 of a spine will now be described. In FIG. 8, first and second anchor/guides 12, 18 have been inserted through a minimally invasive incision 20 formed in a patient's skin 22 and are threadably secured into the pedicle areas of adjacent vertebrae 14, 16 as known in the art. The second ends 44 of the guides 18 extend outwardly from the vertebrae 14, 16 and protrude from the incision 20. With the ends of the channels 40 proximate the second ends 44 of the guides 18 accessible outside the surgical site, a flexible cord 26 may be directed through the channels 40 of the respective guides 18 and through a flexible spacer 24 positioned between the guides 18, as depicted in FIG. 9. Due to the flexible nature of the guides 18, any convergence of the longitudinal axes of the pedicle screws 12 does not hinder installation of the spacer 24, since the flexible guides 18 may be deformed to accommodate the spacer 24 without requiring a larger incision. Flexibility of the guides 18 is particularly useful in regions of the lumbar or sacral portions of the spine where curvature of the spine causes significant convergence of the guides that would otherwise present difficulties if the guides were rigid (see FIG. 8A).

Figure 10:
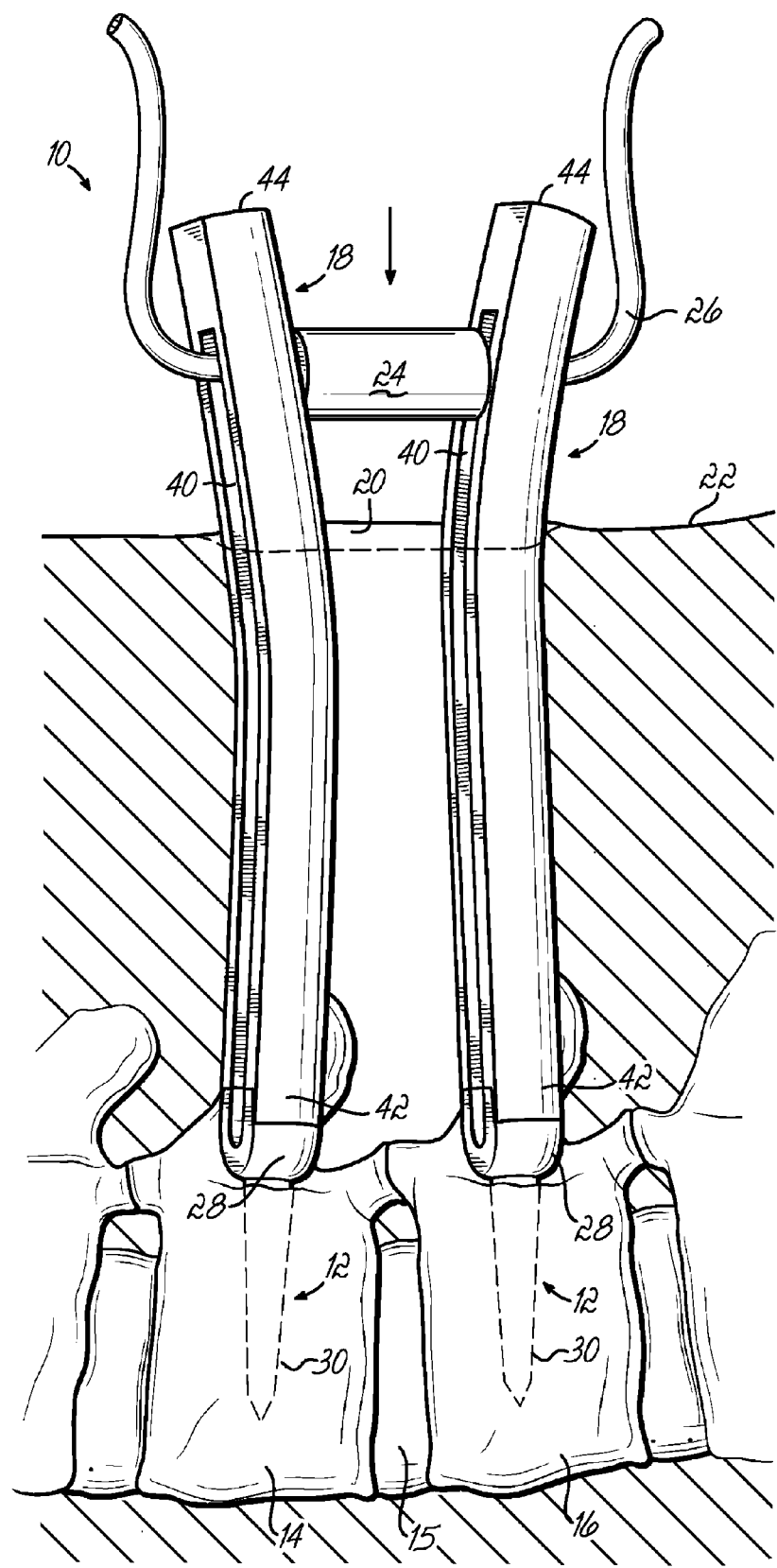
FIG. 10 illustrates the apparatus of FIG. 9 with the spacer being directed along the guides toward the anchors.
Figure 11:
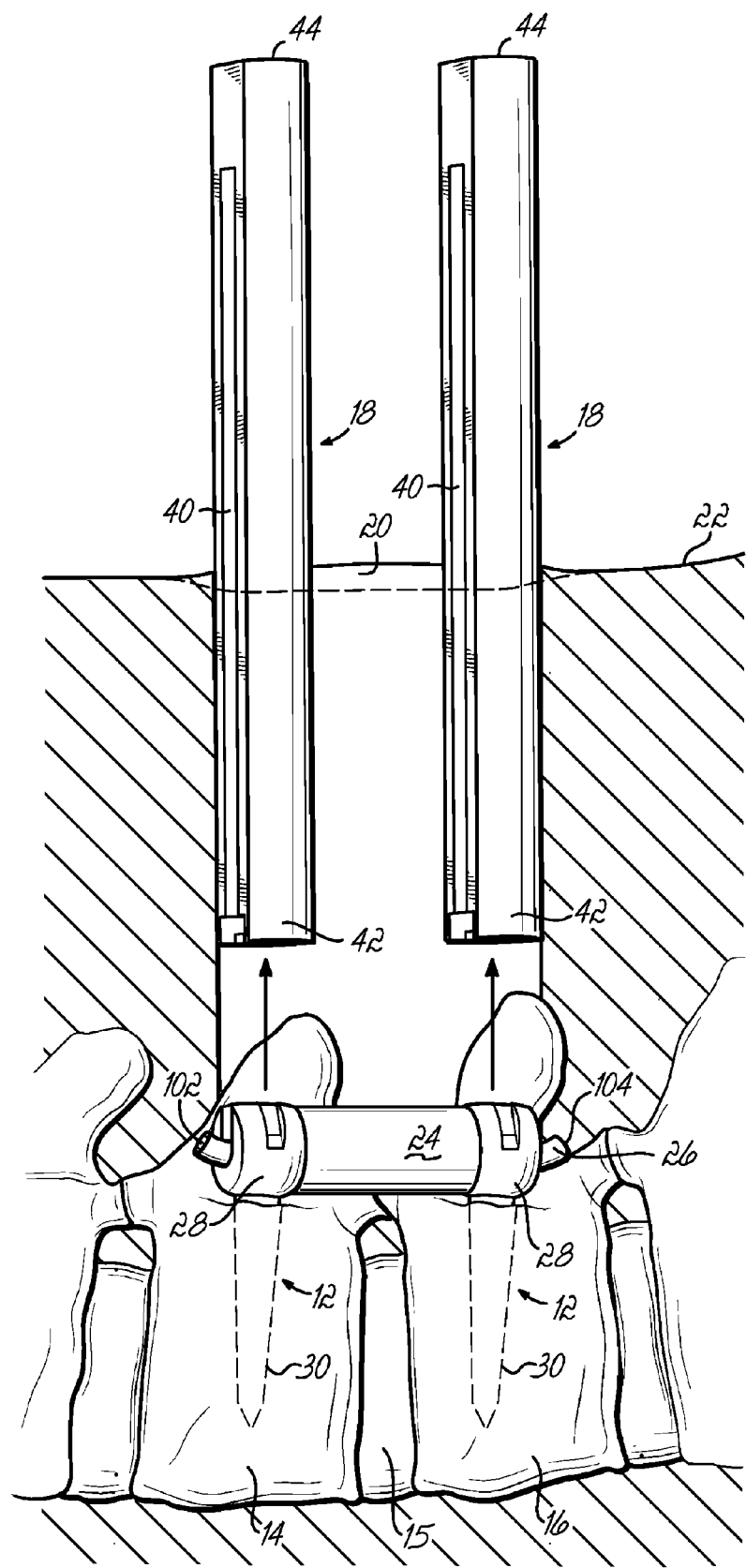
FIG. 11 illustrates the apparatus of FIG. 10 with the spacer installed between the pedicle screws and the guides being removed from the surgical site.

With the spacer 24 positioned between the guides 18 and the cord 26 extending through the respective channels 40, as illustrated in FIG. 10, the spacer 24 and cord 26 may be directed downwardly through the incision 20 to an installation position between the pedicle screws 12, as depicted in FIG. 1. Once the spacer 24 is in position, the securing member, such as set screw 72, may be engaged by a driver 100 or other installation tool suitable to dislodge the set screw 72 from the second end 44 of the guide 18. The driver 100 then urges the set screw 72 along the longitudinal length of the guide 18, directed by the grooves 74a, 74b formed in the guide 18, as illustrated in FIGS. 2A and 2B, into engagement with the threaded open end 36 of the head 28 of the pedicle screw 12. Thereafter the set screw 72 may be threadably advanced into the slot 32 of the pedicle screw 12 to engage and secure the cord 26 to the head 28 of the pedicle screw 12. The guides 18 may then be released from the heads 28 of the pedicle screw 12 and withdrawn through the incision 20, as depicted in FIG. 11. The outer ends 102, 104 of the cord 26 may be trimmed and the incision 20 closed to complete the installation.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope or spirit of the general inventive concept

What is claimed is:

1. A spinal stabilization apparatus, comprising:
   a vertebral anchor comprising a head portion, a bone attachment portion, and a central longitudinal axis extending through the head portion and the bone attachment portion;
   a slot in said head portion, said slot having an open end opposite said bone attachment portion;
   an elongate flexible guide having a distal end removably coupled to said head portion of said vertebral anchor and adapted to extend percutaneously from a surgical site to a proximal end, said elongate flexible guide including a distal portion extending along the central longitudinal axis from the distal end to a bend and a proximal portion extending from the bend to the proximal end; and
   a channel in said guide, said channel extending longitudinally of said guide and communicating with said slot through said open end;
   wherein the proximal portion of the elongate flexible guide is disposed at an oblique angle to the central longitudinal axis.

2. The apparatus of claim 1, further comprising:
   an elongate flexible cord having an outer circumference sized to be received within said channel for movement therealong and into said slot through said open end.

3. The apparatus of claim 2, further comprising:
   a securing member configured to be coupled to said head portion and to retain said cord within said slot when coupled thereto.

4. The apparatus of claim 3, wherein:
said head portion includes internal threads proximate said open end; and said securing member is a set screw having external threads corresponding to said internal threads of said head portion.

5. The apparatus of claim 2, further comprising:
a spacer removably received on said cord.

6. The apparatus of claim 3, wherein said securing member is removably carried on said guide prior to engagement with said head portion.

7. The apparatus of claim 6, wherein said channel of said guide is adapted to direct said securing member along said channel for engagement with said head portion.

8. The apparatus of claim 1, wherein said guide is flexible and comprises polymeric material.

9. The apparatus of claim 8 wherein said polymeric material is integrally molded onto said head portion.

10. The apparatus of claim 8 wherein said polymeric material is adhesively bonded to said head portion.

11. The spinal stabilization apparatus of claim 1, wherein the proximal portion of the elongate flexible guide is at an oblique angle to the distal portion of the elongate flexible guide.

12. The spinal stabilization apparatus of claim 1, further comprising:
a second vertebral anchor comprising a bone attachment portion and a head portion including a slot having an open end opposite said bone attachment portion; and
a second elongate guide removably coupled to said head portion of said second vertebral anchor and adapted to extend percutaneously from a surgical site;
wherein the distal portion of the elongate flexible guide is removably coupled to the vertebral anchor and a distal portion of the second elongate guide is removably coupled to the second vertebral anchor;
wherein the distance between the distal portion of the elongate flexible guide and the distal portion of the second elongate guide is less than the distance between the proximal portion of the elongate flexible guide and a proximal portion of the second elongate guide.

13. The spinal stabilization apparatus of claim 12, wherein the distal portion of the elongate flexible guide converges toward the second elongate guide in a direction away from the vertebral anchor.

14. A spinal stabilization apparatus, comprising:
a vertebral anchor comprising a head portion and a bone attachment portion;
a slot in said head portion, said slot having an open end opposite said bone attachment portion;
an elongate flexible guide removably coupled to said head portion of said vertebral anchor and adapted to extend percutaneously from a surgical site, said elongate flexible guide includes a bend between a proximal portion and a distal portion of the elongate flexible guide; and
a channel in said guide, said channel extending longitudinally of said guide and communicating with said slot through said open end;
wherein said guide is flexible and comprises polymeric material; and
wherein at least part of said guide proximate said head portion comprises non-polymeric material.

15. The apparatus of claim 14, wherein said non-polymeric portion of said guide is removably coupled to said head portion.

16. The apparatus of claim 14, wherein:
said head portion includes first screw threads proximate said open end; and
said non-polymeric portion of said guide includes second screw threads complementary to said first screw threads of said head portion, said first and second screw threads cooperating to removably couple said guide to said head portion.

17. An implantable spinal apparatus, comprising:
at least first and second vertebral anchors, each said vertebral anchor comprising a head portion and a bone attachment portion;
each said head portion including a slot having an open end opposite said bone attachment portion;
a plurality of elongate flexible guides, each guide including a proximal end and a distal end, each guide having an uncoupled state and a coupled state, each guide associated with one of said vertebral anchors and having said distal end of said guide removably coupled to said head portion of said respectively associated vertebral anchor, each guide including a bend along the length of said guide such that the distance between the proximal ends of the elongate guides is greater than the distance between the distal ends of the elongate guides while the elongate guides are in the coupled state;
wherein each guide is in the uncoupled state before being coupled to the respectively associated vertebral anchor and each guide is in the coupled state after being coupled to the respectively associated vertebral anchor;
each said guide including a channel extending longitudinally of said guide and communicating with said slot of said respective vertebral anchor through said open end of said head portion;
an elongate flexible cord having an outer circumference sized to be received within said channels of said guides for movement therealong and into said slots of said vertebral anchors through said respective open ends of said head portions;
a spacer removably received on said cord; and
a plurality of securing members, each securing member associated with one of said vertebral anchors and configured to be coupled to said respective head portion and to retain said cord within said respective slot.

18. A method of stabilizing a spine through an incision, comprising:
securing at least first and second anchors to respective first and second vertebrae, each anchor including a bone attachment portion and a head having a slot having an open end opposite the bone attachment portion;
detachably coupling a first elongate flexible guide to the head of the first anchor such that a channel of the first elongate flexible guide communicates with the slot in the head of the first anchor;
detachably coupling a second elongate flexible guide to the head of the second anchor such that a channel of the second elongate flexible guide communicates with the slot in the head of the second anchor;
coupling a spacer to an elongate cord;
directing a first portion of the cord into the channel of the first elongate flexible guide exterior of the incision and a second portion of the cord into the channel of the second elongate flexible guide exterior of the incision such that the spacer is located between the guides;
flexing the guides to receive the spacer therebetween, the flexing occurring after the first and second flexible elongate guides have been coupled to the first and second anchors, respectively;
directing the cord and spacer along the guides to an installation position between the heads of the anchors; and
removing the guides from the heads of the anchors.

19. The method of claim 18, further comprising:
securing the cord to the heads of the anchors.

20. The method of claim 19, wherein securing the cord comprises threadably engaging a securing member to the respective anchor heads.

21. The method of claim 20 further comprising directing the securing members along the guides to engage the heads of the anchors.

22. An implantable spinal apparatus, comprising:
at least first and second vertebral anchors, each said vertebral anchor comprising a head portion and a bone attachment portion, each said head portion including a slot having an open end opposite said bone attachment portion;
a plurality of elongate guides, each guide including a proximal end and a distal end, each guide associated with one of said vertebral anchors and having said distal end of said guide removably coupled to said head portion of said respectively associated vertebral anchor;
each said guide including a channel extending longitudinally of said guide and communicating with said slot of said respective vertebral anchor through said open end of said head portion;
each said guide including a bend along the length of said guide and a corresponding bend along the length of said channel such that the distance between a center of each of the channels of the elongate guides near the proximal ends of the elongate guides is greater than the distance between the center of each of the channels near the distal ends of the elongate guides while the elongate guides are removably coupled to said head portions of the vertebral anchors;
an elongate flexible cord having an outer circumference sized to be received within said channels of said guides for movement therealong and into said slots of said vertebral anchors through respective open ends of said head portions;
a spacer removeably received on said cord; and
a plurality of securing members, each securing member associated with one of said vertebral anchors and configured to be coupled to said respective head portion and to retain said cord within said respective slot.

23. The implantable spinal apparatus of claim 22, wherein each said securing member is removably carried on a respective one of said guides prior to engagement with said head portion.

24. The implantable spinal apparatus of claim 22, wherein said channel of each said guide is adapted to direct said securing member along said channel for engagement with said head portion.

25. The implantable spinal apparatus of claim 22, wherein
each said head portion includes internal threads proximate said open end; and
said securing members are set screws having external threads corresponding to said internal threads of said head portion.

26. An implantable spinal apparatus, comprising:
at least first and second vertebral anchors, each said vertebral anchor comprising a head portion and a bone attachment portion;
each said head portion including a slot having an open end opposite said bone attachment portion;
a plurality of elongate guides, each guide including a proximal end and a distal end, each guide associated with one of said vertebral anchors and having said distal end of said guide removably coupled to said head portion of said respectively associated vertebral anchors;
each said guide including a channel extending longitudinally of said guide and communicating with said slot of said respective vertebral anchor through said open end of said head portion;
each said guide including a bend along the length of said guide such that the distance between the proximal ends of the elongate guides is greater than the distance between the distal ends of the elongate guides while the elongate guides are removably coupled to said head portions of the vertebral anchors;
an elongate flexible member having an outer circumference sized to be received within said channels of said guides for movement therealong and into said slots of said vertebral anchors through said respective open ends of said head portions; and
a plurality of securing members, each securing member associated with one of said vertebral anchors and configured to be coupled to said respective head portion and to retain said elongate flexible member within said respective slot.

27. The apparatus of claim 26, wherein said elongate flexible member is a flexible cord.

28. A method for implanting a spinal implant through an incision, the method comprising:
obtaining at least first and second anchors, the first and second anchors each including a head portion with a slot having an open end;
coupling the first and second anchors to respective first and second vertebrae;
removably coupling an elongate guide having a proximal end and a distal end to each of the first and second anchors, each elongate guide including a channel extending longitudinally along the guide and communicating with the slot of the respective anchor through the open end of the head portion and each guide including a bend along the length of the guide such that the distance between the proximal ends of the elongate guides is greater than the distance between the distal ends of the elongate guides after the elongate guides have been coupled to the first and second anchors, respectively;
inserting an elongate member into the channel on each of the elongate guides, wherein a flexible spacer is coupled to the elongate member;
moving the elongate member within the channels from the proximal ends to the distal ends;
inserting the elongate member into the slots of the first and second anchors; and
securing the elongate members to the first and second anchors.

29. The method of claim 28, wherein the elongate member is a flexible cord.

* * * * *